US00PP13455P3

(12) United States Plant Patent
Pieters

(10) Patent No.: US PP13,455 P3
(45) Date of Patent: Jan. 7, 2003

(54) CHRYSANTHEMUM PLANT NAMED 'GEDI ONE AVI'

(75) Inventor: Dirk Pieters, Staden (BE)

(73) Assignee: Pieters Plant Production, Bvba, Oostnieuwkerke (BE)

( * ) Notice: Subject to any disclaimer, the term of this patent is extended or adjusted under 35 U.S.C. 154(b) by 0 days.

(21) Appl. No.: 09/873,493

(22) Filed: Jun. 4, 2001

(65) Prior Publication Data

US 2002/0188979 P1 Dec. 12, 2002

(51) Int. Cl.[7] ..... A01H 5/00
(52) U.S. Cl. ..... Plt./289
(58) Field of Search ..... Plt./289, 286, 295

(56) References Cited

U.S. PATENT DOCUMENTS

| | | | | |
|---|---|---|---|---|
| PP10,208 P | | 1/1998 | Pieters | Plt./289 |
| PP10,215 P | * | 1/1998 | Pieters | Plt./289 |
| PP10,216 P | | 1/1998 | Pieters | Plt./290 |
| PP10,463 P | | 6/1998 | Wain | Plt./289 |

* cited by examiner

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant variety characterized by a Large decorative type inflorescence, consistent flowering response to short days, blooming consistently after 49 days of short day length, free branching habit, and consistent natural season flowering habit during the first two weeks of September.

1 Drawing Sheet

LATIN NAME

*Dendranthema morifolium.*

VARIETY

Figure 1:
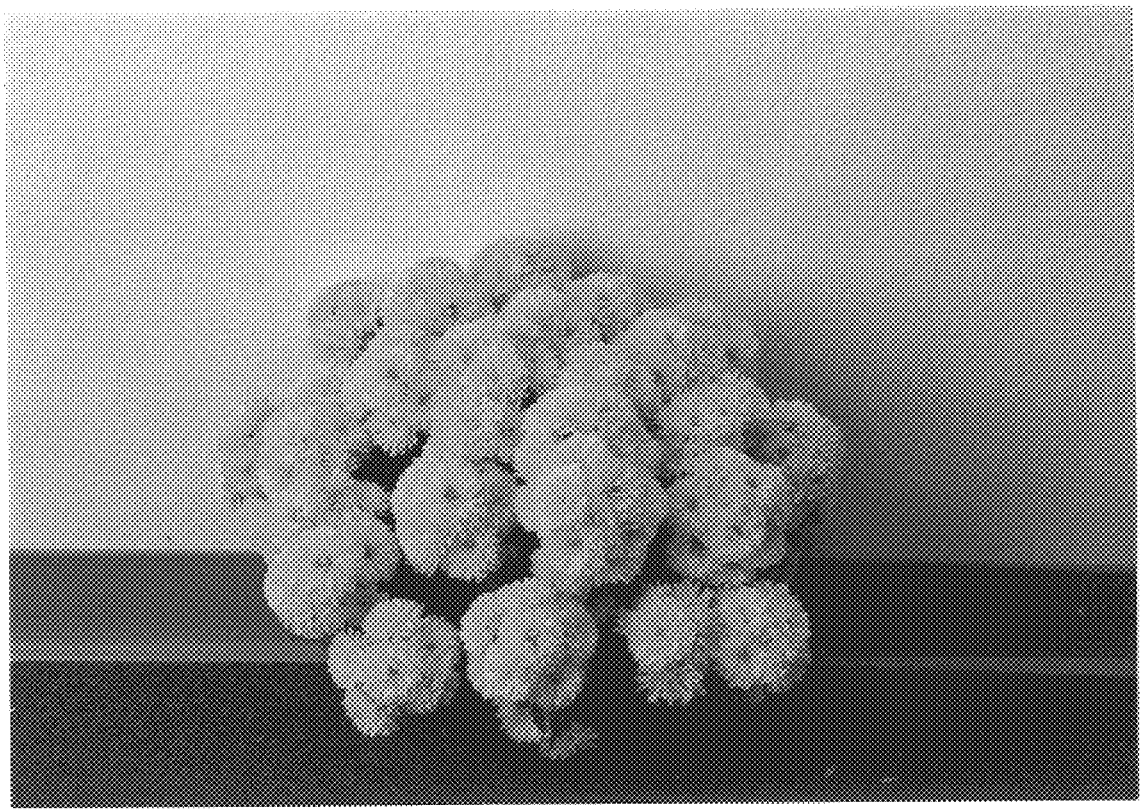

'GEDI ONE AVI'.

BACKGROUND OF THE INVENTION

The present invention relates to a new and distinct cultivar of Chrysanthemum plant, herein after referred to by the cultivar name 'GEDI ONE AVI'. This new cultivar originated from hybridization of a female Chrysanthemum plant cultivar 'Pinos' (U.S. Plant Pat. No. 10,208) with a male Chrysanthemum plant cultivar 'Dark Veria' (U.S. Plant Pat. No. 10,215). The new cultivar was discovered by the inventor in October 1997.

Asexual reproduction of the new cultivar by apical tip cutting and meristem tissue culture was performed in Oxnard, Calif. and has shown that the unique features of this new cultivar are stable and reproduced true to type on successive generations.

SUMMARY OF THE INVENTION

The cultivar 'GEDI ONE AVI' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GEDI ONE AVI'. These characteristics in combination distinguish 'GEDI ONE AVI' as a new and distinct Chrysanthemum:

1. Large decorative type inflorescence;

2. Consistent flowering response to short days, blooming consistently after 49 days of short day length;

3. Free branching habit; and

4. Consistent natural season flowering habit during the first two weeks of September.

Plants of the new cultivar are similar to plants of the parent cultivar, 'Pinos', in most horticultural characteristics, however plants of the new cultivar differed from plants of the cultivar 'Pinos' in the following characteristics:

1. The new cultivar has a wider diameter flower;

2. The new cultivar is taller and wider.

Plants of the new cultivar are similar to plants of the parent cultivar, 'Dark Veria', in most horticultural characteristics, however plants of the new cultivar differed from plants of the cultivar 'Dark Veria' in the following characteristics:

1. The new cultivar has a wider diameter flower;

2. The new cultivar has many more ray florets than the parent;

3. The new cultivar naturally blooms three weeks earlier; and

4. The new cultivar is taller and wider.

The new cultivar can be compared to the Chrysanthemum cultivar 'CLEAGAR GF1' (disclosed in U.S. Plant Pat. No. 10,463). However plants of the new Chrysanthemum differed from the plants of the cultivar 'CLEAGAR GF1' in the following characteristics:

1. New cultivar naturally blooms 2 weeks earlier;

2. New cultivar has larger diameter blooms;

3. New cultivar has more blooms per flowering branch; and

4. New cultivar is taller and wider.

BRIEF DESCRIPTION OF THE PHOTOGRAPHS

The photograph shows a plant of 'GEDI ONE AVI' grown in a 6-inch container. A single cutting was used in the container.

DETAILED BOTANICAL DESCRIPTION

In the following description, color references are made to The Royal Horticultural Society Colour Chart except where general terms of ordinary dictionary significance are used. The following observations and measurements describe plants grown in a commercial field on Oxnard, Calif. in the month of September 2000. The growing conditions range from 60° to 65° F. at night to 70° to 85° F. during the day. Measurements and numerical values represent averages of typical flowering types.

Botanical classification: *Dendranthema morifolium* cultivar 'GEDI ONE AVI'.
Commercial classification: Garden-type Chrysanthemum.
Parentage: Hybridization of female parent 'Pinos' (U.S. Plant Pat. No. 10,208) with male parent 'Dark Veria' (U.S. Plant Pat. No. 10,215).

PROPAGATION

Time to rooting: 7 to 14 days at approximately 21° C.
Root description: Fine fibrous.

PLANT

Growth habit: Mounding herbaceous perennial.
Height: Approximately 27.5 cm.
Plant spread: Approximately 28 cm.
Growth rate: Moderate.
Branching characteristics: Free branching.
Length of lateral branches: Approximately 23 cm.
Number of leaves per lateral branch: Approximately 26.

FOLIAGE

Leaf:
- *Arrangement.*—Alternate single.
- *Average length.*—Approximately 5.6 cm.
- *Average width.*—Approximately 3.4 cm.
- *Shape of blade.*—Pinnately lobed and toothed.
- *Apex.*—Acuminate.
- *Base.*—Attenuate.
- *Attachment.*—Stalked.
- *Margin.*—Serrate.
- *Texture of top surface.*—Lightly pubescent.
- *Texture of bottom surface.*—Lightly pubescent.
- *Color.*—Young foliage upper side: Near 147A. Young foliage under side: Near 147B. Mature foliage upper side: Near 147A. Mature foliage under side: Near 147B. Venation upper side: Near 147B. Venation under side: Near 147B.

Petiole:
- *Average length.*—Approximately 2.0 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately the first two weeks of September.
- *Number of inflorescences per stem.*—Approximately 12.
- *Inflorescence diameter.*—Approximately 5.3 cm.
- *Inflorescence depth.*—Approximately 2.0 cm.
- *Inflorescence longevity on plant.*—Approximately 22–24 days.
- *Persistence.*—Persistent.

Ray florets:
- *Appearance.*—Matte.
- *Texture.*—Smooth.
- *Average number per flower.*—Approximately 190.
- *Shape.*—Cylindric.
- *Margin.*—Entire.
- *Apex.*—Obtuse.
- *Length.*—Approximately 1.8 cm.
- *Width.*—Approximately 0.5 cm.
- *Color.*—Upper surface at first opening: Near 14A. Upper surface at maturity: Near 7B. Upper surface at fading: Near 7C. Under surface at first opening: Near 14B. Under surface at maturity: Near 7C. Under surface at fading: Near 7D.

Disc florets:
- *Appearance.*—Shiny.
- *Texture.*—Smooth.
- *Average number per flower.*—Approximately 35.
- *Shape.*—Cylindric.
- *Apex.*—Obtuse.
- *Average length.*—Approximately 0.3 cm.
- *Average width.*—Approximately 0.1 cm.
- *Color.*—At first opening: Near 21A. At maturity: Near 15A. At fading: Near 13A.

Peduncle:
- *Length.*—At terminal end (shortest): Approximately 2.3 cm. At lateral end (longest): Approximately 3.5 cm.
- *Strength.*—Moderate.
- *Color.*—Near 146A.
- *Habit.*—Erect.

Inflorescence bud:
- *Length.*—Approximately 0.5 cm.
- *Diameter.*—Approximately 0.5 cm.
- *Form.*—Globular.
- *Color.*—Near 12A.

Phyllaries:
- *Appearance.*—Matte.
- *Texture.*—Lightly pubescent.
- *Number.*—Approximately 30 to 40.
- *Shape.*—Ovate.
- *Margin.*—Entire.
- *Apex.*—Acute.
- *Color.*—Upper side: Near 137B. Under side: Near 137B.
- *Size of involucral bracts.*—Approximately 0.5 cm wide by Approximately 0.7 cm long.

Reproductive organs:
- *Ray florets.*—Pistillate: Number of pistils per flower: 1. Stigma shape: 2 branched. Stigma color: Near 15A. Stigma Length: Approximately 0.1. Style color: Near 144B. Style length: Approximately 0.3 cm.
- *Disc florets.*—Number of pistils per disc flower: 1. Stigma shape: Cylindric. Style length: Approximately 0.1 cm. Number of stamens per disc flower: Approximately 5. Anther shape: Tubular. Anther color: Near 15A. Pollen color: Near 15A.

OTHER CHARACTERISTICS

Disease resistance: Neither resistance nor susceptibility observed.
Seed production: Commercially, this plant is not used or observed in a stage wherein seeds would be produced. Therefore, seed production has not been observed.

What is claimed is:

1. A new and distinct variety of Chrysanthemum plant named 'GEDI ONE AVI' as herein illustrated and described.

* * * * *